United States Patent
Liang et al.

(10) Patent No.: US 11,681,054 B2
(45) Date of Patent: Jun. 20, 2023

(54) POSITION-SIGNAL PROCESSING METHOD FOR FLAT PANEL GAMMA IMAGING PROBE

(71) Applicant: Institute of Nuclear Energy Research, Atomic Energy Council, Executive Yuan, R.O.C, Taoyuan (TW)

(72) Inventors: Hsin-Chin Liang, Taoyuan (TW); Chen-Han Cheng, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 70 days.

(21) Appl. No.: 17/529,449

(22) Filed: Nov. 18, 2021

(65) Prior Publication Data

US 2023/0047770 A1 Feb. 16, 2023

(30) Foreign Application Priority Data

Aug. 5, 2021 (TW) .................................. 110128913

(51) Int. Cl.
G01T 1/166 (2006.01)
G01T 1/164 (2006.01)
A61B 6/00 (2006.01)
A61B 6/03 (2006.01)

(52) U.S. Cl.
CPC ............ G01T 1/166 (2013.01); G01T 1/1644 (2013.01); *A61B 6/037* (2013.01); *A61B 6/4258* (2013.01)

(58) Field of Classification Search
CPC ..... G01T 1/166; G01T 1/1644; G01T 1/1647; G01T 1/1642; A61B 6/037; A61B 6/4258
See application file for complete search history.

(56) References Cited

U.S. PATENT DOCUMENTS

2007/0242867 A1\* 10/2007 Jan .................... G06T 11/006
382/154

FOREIGN PATENT DOCUMENTS

TW I337329 B 2/2011

OTHER PUBLICATIONS

Hsin-Chin Liang et al., Study of A Position Decoding Method Making Imaging area Continuous for A Planar Positron Imaging Probe, FASMI 2020 conference, 2020, Institute of Nuclear Energy Research / Health Physics Division, Taoyuan, Taiwan.

\* cited by examiner

*Primary Examiner* — David P Porta
*Assistant Examiner* — Gisselle M Gutierrez
(74) *Attorney, Agent, or Firm* — Locke Lord LLP; Tim Tingkang Xia, Esq.

(57) ABSTRACT

A position-signal processing method for flat panel gamma imaging probe includes a modeling phase and a use phase. In the modeling phase, a weight direction for an imaging detector is defined, position centers and weight ratios of the imaging detector in the weight direction are utilized to obtain a distribution graph of the weight ratios to the position centers, and curve fitting is performed upon the distribution graph to obtain a position estimation curve. In the use phase, the position estimation curve is utilized to derive a position estimation value of a probe trigger event in a 2D crystal diagram, a position value of the probe in the 2D crystal diagram with respect to the position estimation value of the probe trigger event is obtained, and a crystal code is located in a crystal code look-up table for the position value of the probe in the 2D crystal diagram.

14 Claims, 9 Drawing Sheets

POSITION-SIGNAL PROCESSING METHOD FOR FLAT PANEL GAMMA IMAGING PROBE

CROSS REFERENCE TO RELATED APPLICATION

This application claims the benefits of Taiwan application Serial No. 110128913, filed on Aug. 5, 2021, the disclosures of which are incorporated by references herein in its entirety.

TECHNICAL FIELD

The present disclosure relates in general to a position-signal processing method for flat panel gamma imaging probe.

BACKGROUND

In the art, in order to meet requirements in imaging field and space, the conventional nuclear medicine scanning technology generally integrates multiple imaging detectors to match a planar imaging probe. However, if the imaging space needs to be larger, the planar imaging probe shall be made bigger as well, but a need of more equipment occupation would be arise. Namely, while more imaging detectors are required to satisfy a larger imaging space, more equipment expense is inevitable. Nevertheless, a sliding scan strategy is introduced to provide more scanning rooms by enhancing mobility of the imaging probe. Thereupon, problems in equipment occupation and cost can be resolved simultaneously.

However, in the sliding scan strategy, since the entire image is formed by integrating individual images provided by the discrete imaging detectors, thus a relevant calculation algorithm is needed to maintain the image with an acceptable and consistent resolution. For example, in one of conventional calculation algorithms, such as Anger's logic algorithm, following equations (1) and (2) are provided.

$$x = (x^+ - x^-)/(x^+ + x^-) \quad (1)$$

$$y = (y^+ - y^-)/(y^+ + y^-) \quad (2)$$

In these two equations (1) and (2), x and y stand for positions in the X and Y directions, respectively; $x^+$, $x^-$, $y^+$, $y^-$ stand for signals with position information in the X and Y directions; $(x^+ + x^-)$ stands for a total energy in the X direction; and, $(y^+ + y^-)$ stands for a total energy in the Y direction. It is obvious that, in the conventional technology, position and energy are directly related. However, empirically, the conventional calculations are acceptable in the middle portion of each of the imaging detectors, but would present considerable errors at the boundary thereof. As such, this sliding scan strategy couldn't handle well in processing information from junctions of the imaging detectors. In addition, while the conventional technology is applied to photoelectric semiconductor elements, signals of the imaging detectors may shift or fluctuate due to the instinct temperature-sensitive characteristics of this type of elements (hereinafter, the temperature-sensitive effect); i.e., fluctuations in total energy. As a consequence, results of the position calculations would fluctuate as well, the overall imaging output would become unstable, and thus performance of the probe with respect to these photoelectric semiconductor elements would be downgraded.

Hence, how to improve the problems encountered above will be one of the issues that the related industry has to solve.

SUMMARY

An object of the present disclosure is to provide a position-signal processing method for flat panel gamma imaging probe that can resolve problems in junction areas of adjacent imaging detectors, such that the imaging probe can present an entire and continuous imaging area with the temperature-sensitive effect to be effectively reduced for ensuring high-performance and stable output at the corresponding imaging probe.

In this disclosure, a position-signal processing method for flat panel gamma imaging probe includes a modeling phase and a use phase. In the modeling phase, at least the following steps are included: defining a weight direction for a single imaging detector; according to position centers and weight ratios of the single imaging detector in an X direction and a Y direction of the weight direction to obtain a distribution graph of the weight ratios with respect to the position centers; and, performing curve fitting upon the distribution graph of the weight ratios with respect to the position centers to obtain a position estimation curve related to the weight ratios. In the use phase, at least the following steps are included: utilizing the position estimation curve obtained in the modeling phase to derive a position estimation value of a trigger event of a probe in a 2D crystal diagram; obtaining a position value of the probe in the 2D crystal diagram with respect to the position estimation value of the trigger event; and, locating a crystal code in a crystal code look-up table with respect to the position value of the probe in the 2D crystal diagram for a following image-reconstructing calculation.

In one embodiment of this disclosure, prior to the step of obtaining the position value of the probe in the 2D crystal diagram with respect to the position estimation value of the trigger event, the position-signal processing method for flat panel gamma imaging probe further includes a step of performing a position-correcting calculation upon the position value.

In one embodiment of this disclosure, the position-correcting calculation is performed upon an energy value of the single imaging detector and an energy value of an imaging detector adjacent to the single imaging detector.

In one embodiment of this disclosure, prior to the step of performing the position-correcting calculation upon the position value, the position-signal processing method for flat panel gamma imaging probe further includes the steps of: determining whether or not a weight ratio falls within a split-value area; if negative, performing the position-correcting calculation upon the position value; and. if positive, obtaining the position value of the probe in the 2D crystal diagram with respect to the position estimation value of the trigger event.

As stated, in the position-signal processing method for flat panel gamma imaging probe provided by this disclosure, the position decoding algorithm does not follow the conventional technology (i.e., Anger's logic), and the problem of discontinuous imaging in the junction area of the adjacent imaging detectors in the conventional technology can be resolved. Thereupon, the entire imaging area can be complete, continuous and consistent in maintaining the high resolution.

In addition, the position-signal processing method for flat panel gamma imaging probe provided by this disclosure can lessen the temperature-sensitive effect, and can stabilize the high-performance output of the imaging probe assembly.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
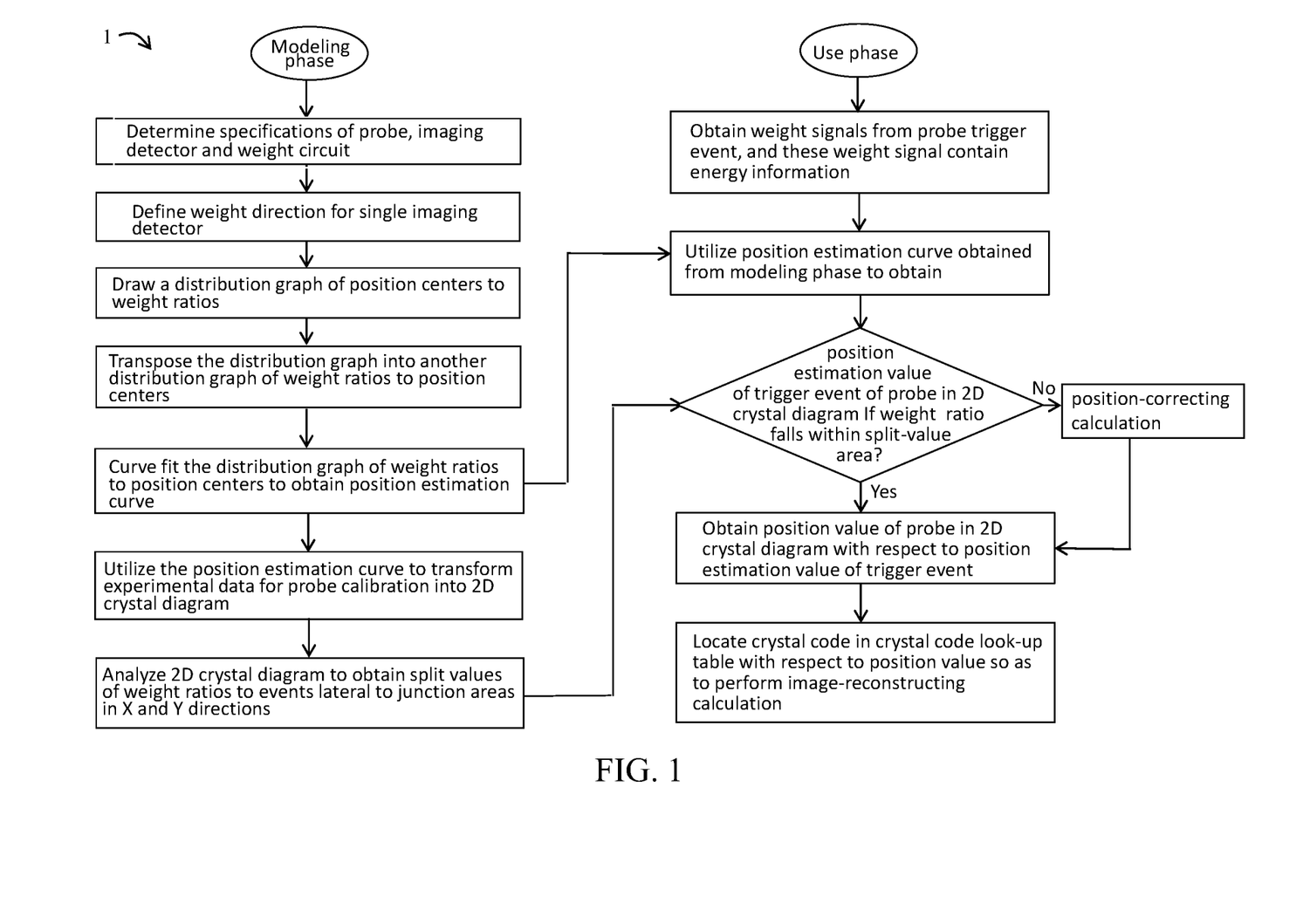
FIG. 1 is a schematic flowchart of an embodiment of the position-signal processing method for flat panel gamma imaging probe in accordance with this disclosure.

It shall be explained that, in this disclosure, an application of a flat panel proton imaging device for brain scanning is implemented as a typical example for explaining details of the disclosure. Referring now to FIG. 1, a schematic flowchart of an embodiment of the position-signal processing method for flat panel gamma imaging probe in accordance with this disclosure is shown. This embodiment is particularly applicable for a super-resolution algorithm upon pixels with crystal size □1.1 mm; i.e., each of photonic pixels is arranged to have a plurality of crystals (9 or more). In this embodiment, the position-signal processing method for flat panel gamma imaging probe includes two phases: a modeling phase and a use phase.

In the modeling phase, specification of an imaging probe (hereinafter called as the probe) shall be determined firstly. The probe includes imaging detectors and associated weight circuits. The imaging detector of this embodiment is a gamma-ray detector consisted of a plurality of scintillating crystals formed into a matrix format. The weight circuit for the imaging detector is a circuit capable of reading bidirectional signals (in an X direction and a Y direction). In each of gamma-ray incidence events, four position signals ($x^+$, $x^-$, $y^+$, $y^-$) are obtained to form energy information of the this incidence event.

The probe of a planar scan unit is consisted of a plurality of imaging detectors. In the art, a conventional probe can only provide a 2D proton image. However, according to this disclosure, the probe of the planar scan unit can utilize a 2D image obtained through a static scan without rotating the probe to produce a 3D tomography.

Figure 2:
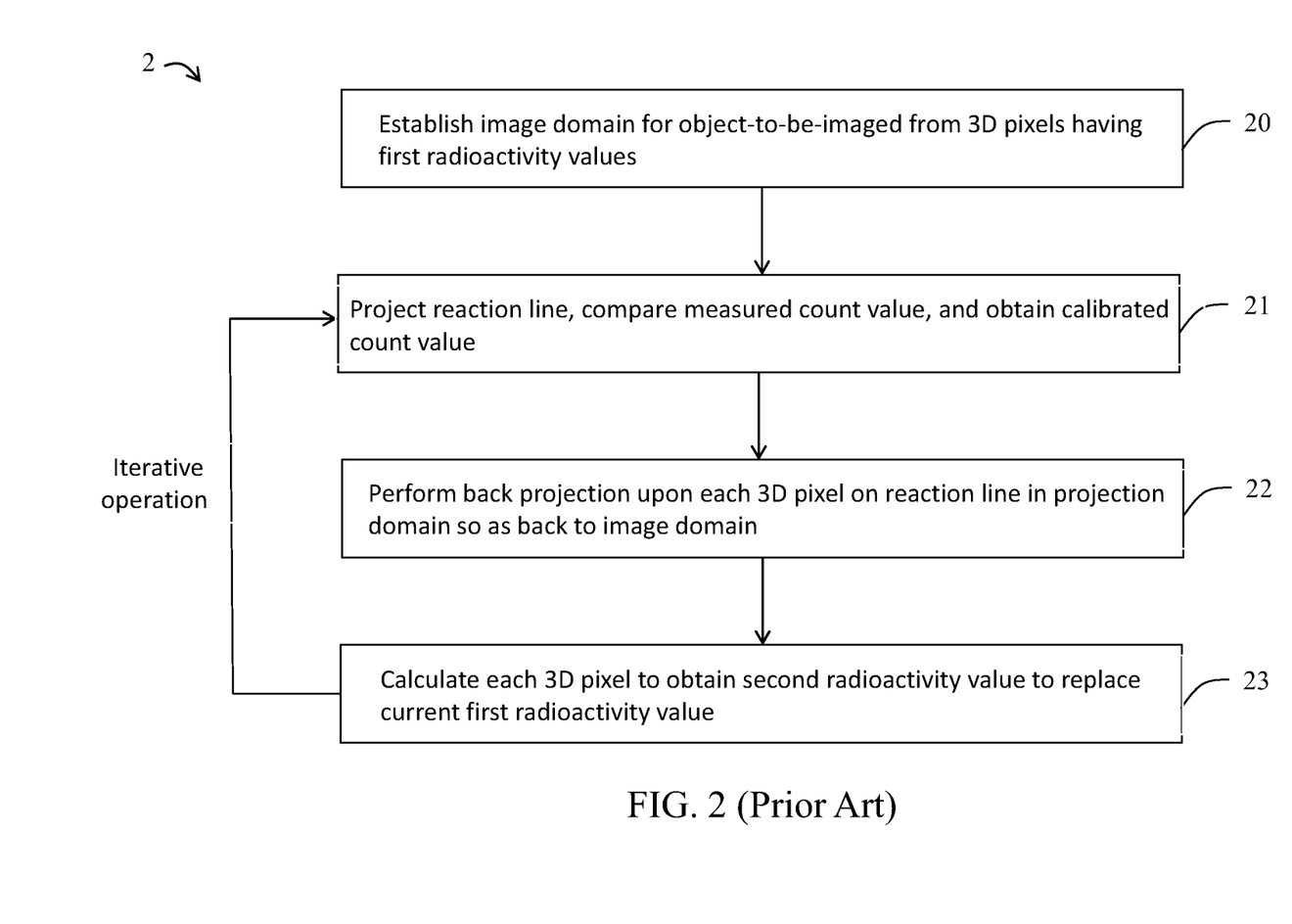
FIG. 2 is a schematic flowchart of a conventional image reconstruction method for structuring two-dimensional planar imaging into three-dimensional imaging.
Figure 3:
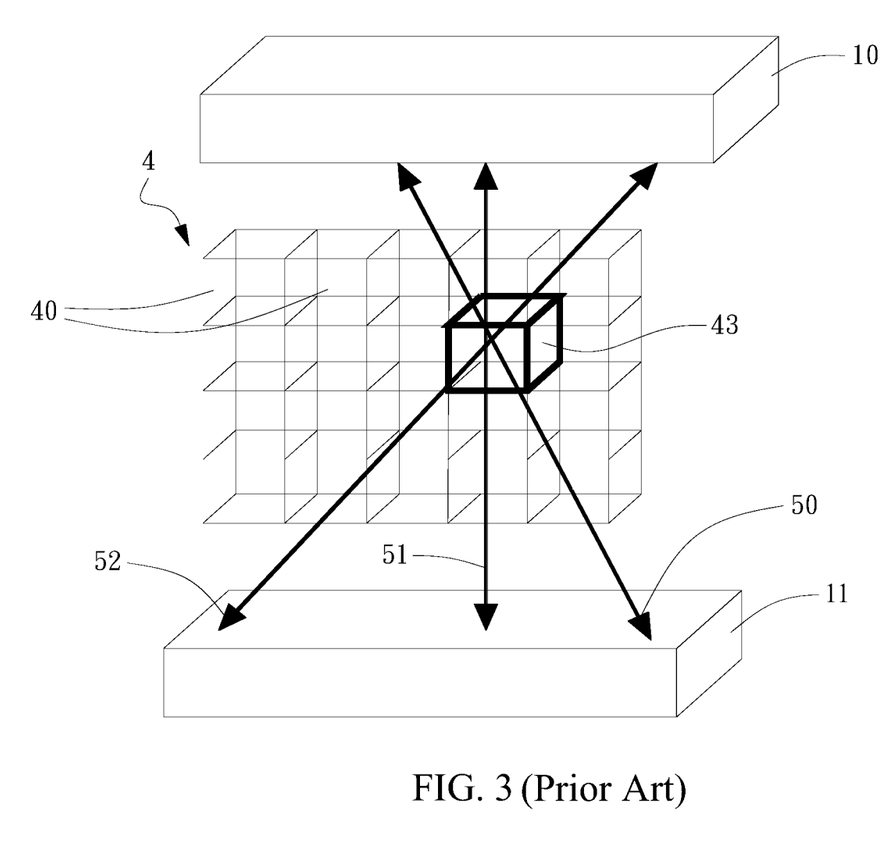
FIG. 3 is a schematic view showing a typical image domain for FIG. 2.

In particular, this embodiment of FIG. 1 integrates the image reconstruction method for structuring two-dimensional planar imaging into three-dimensional imaging of Taiwan Patent Pub. No. 1337329. Referring to FIG. 2, the image reconstruction method for structuring two-dimensional planar imaging into three-dimensional imaging 2 is mainly to reconstruct an image by processing a plurality of reaction lines generated by projecting an object-to-be-imaged, in which each of the reaction lines is corresponding to a measured count value. The image reconstruction method 2 includes Step 20 to Step 23 as follows. Firstly, in performing Step 20, a plurality of 3D pixels (also called as voxels) are utilized to construct an image domain with respect to the object-to-be-imaged, in which each of the 3D pixels has a first radioactivity value. Referring to FIG. 3, a typical image domain for FIG. 2 is schematically shown. In this embodiment, the imaging detectors include a first detector 10 and a second detector 11, and the object-to-be-imaged is disposed between the first detector 10 and the second detector 11. The object-to-be-imaged is divided into a plurality of 3D pixels 40 so as to construct an image domain 4. In the image domain 4, each of the 3D pixels 40 has a first radioactivity value standing for intensity of radioactivity. For example, to the 3D pixel 43, reaction lines 50, 51 and 52 stand for different radiation events. Then, in Step 21, individual projection is performed along each of the reaction lines, and a corresponding projection result is compared with a measured count value so as to obtain a calibrated count value for the respective reaction line. Practically, the measured count value is provided by the detectors, the projection of the 3D pixel to the projection domain provides an estimated count value, and the estimated count value can be compared with the measured count value so as to obtain the calibrated count value. Then, in Step 22, according to the relationship between the calibrated count value and the first radioactivity value along the reaction line of the 3D pixel in the projection domain, a back projection is performed back to the image domain, such that a weight value for the 3D pixel can be derived by evaluating the first radioactivity value along the reaction line of the 3D pixel and the corresponding estimated count value. The weight value can be a ratio of the first radioactivity value along the reaction line of the 3D pixel to the estimated count value. According to the weight value along the reaction line of the 3D pixel, the back projection is performed to reconstruct the image domain. Then, in Step 23, by evaluating a relationship between the calibrated count value and the first radioactivity value of the 3D pixel, a second radioactivity value can be derived to update the first radioactivity value along the reaction line of the 3D pixel. Namely, the second radioactivity value is used to replace the preceding first radioactivity value before the next operation can be performed. In this method 2, a product value can be obtained by having the weight value of the 3D pixel along the reaction line to multiply the corresponding calibrated count value, and then the product value is accumulated to the second radioactivity value for the same reaction line. Finally, Step 21 to Step 23 are repeatedly performed. Namely, an iterative method is applied to carry out multiple operations, including the projection and the back projection, between the image domain 4 and the projection domain. Thereupon, an image can be gradually reconstructed. That is, the interactive method is repeatedly performed so as to reconstruct the image. Thus, the object of utilizing the 2D imaging to derive the 3D tomography can be achieved. Hence, even the flat panel proton imaging device for brain scanning (hereinafter, the planar PET) can be sufficient to provide the 3D tomography. Thus, the planar PET can be applied as the imaging device of this disclosure.

Referring back to FIG. 1, after the specifications of the probe, the imaging detectors and the weight circuits are determined, then the weight direction with respect to the specific imaging detector can be defined; for example, either the X direction or the Y direction. Then, according to X-directional and Y-directional position centers (i.e., position centers of the photo-sensing element in the photoelectric element) and the corresponding weight ratios (based on the specification of the weight circuit) in a single imaging detector, a distribution graph of the weight ratios with respect to the position centers can be obtained. In the distribution graph of the directional position centers vs the weight ratios, the X-directional or Y-directional position centers and the corresponding weight ratios for a single imaging detector are demonstrated. Also, Table 1 lists the distribution relationship between the the X-directional position centers (photoelectric elements in the X direction of the imaging detector) and the weight ratio for each row/column of this exemplary example.

TABLE 1

| Row/Column | $x^+$ position weight | $x^-$ position weight | $x^-/x^+$ weight ratio |
| --- | --- | --- | --- |
| 1 | 1 | 0.0833 | 0.0833 |
| 2 | 0.9091 | 0.165 | 0.1834 |
| 3 | 0.8333 | 0.2483 | 0.3 |
| 4 | 0.75 | 0.3311 | 0.4444 |
| 5 | 0.6637 | 0.4167 | 0.6278 |
| 6 | 0.5882 | 0.5 | 0.8501 |
| 7 | 0.5 | 0.5882 | 1.1764 |
| 8 | 0.4167 | 0.6637 | 1.5928 |
| 9 | 0.3333 | 0.75 | 2.2652 |
| 10 | 0.25 | 0.8333 | 3.356 |
| 11 | 0.1667 | 0.9091 | 5.5097 |
| 12 | 0.0833 | 1 | 12.0048 |

Figure 4:
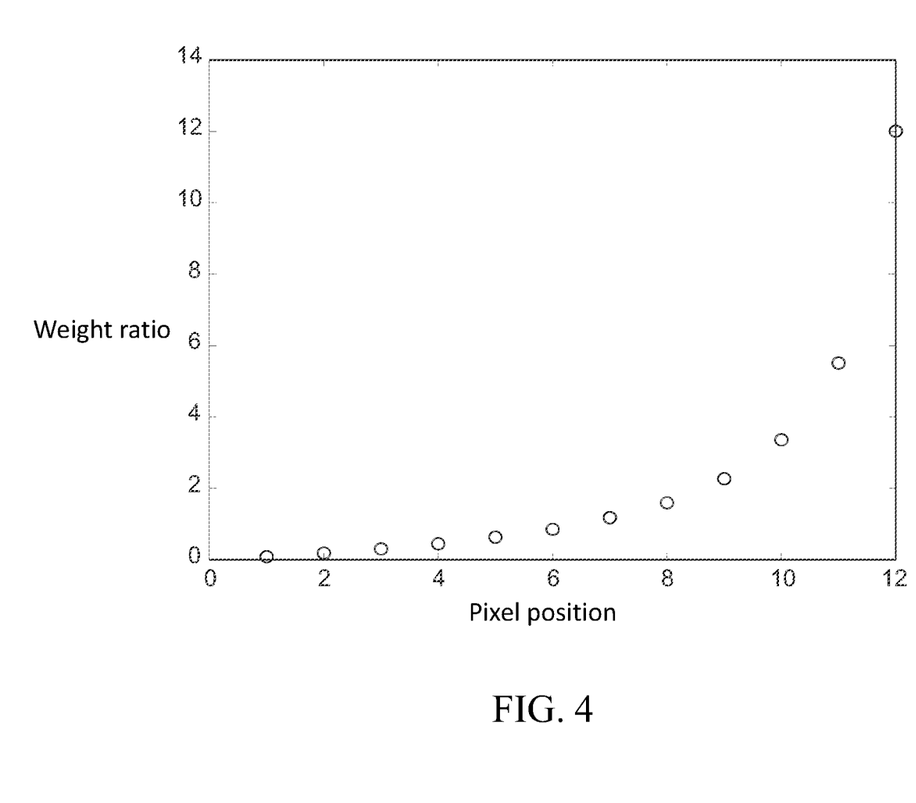
FIG. 4 is a schematic distribution graph of position centers vs weight ratios in an exemplary example in accordance with this disclosure.
Figure 5:
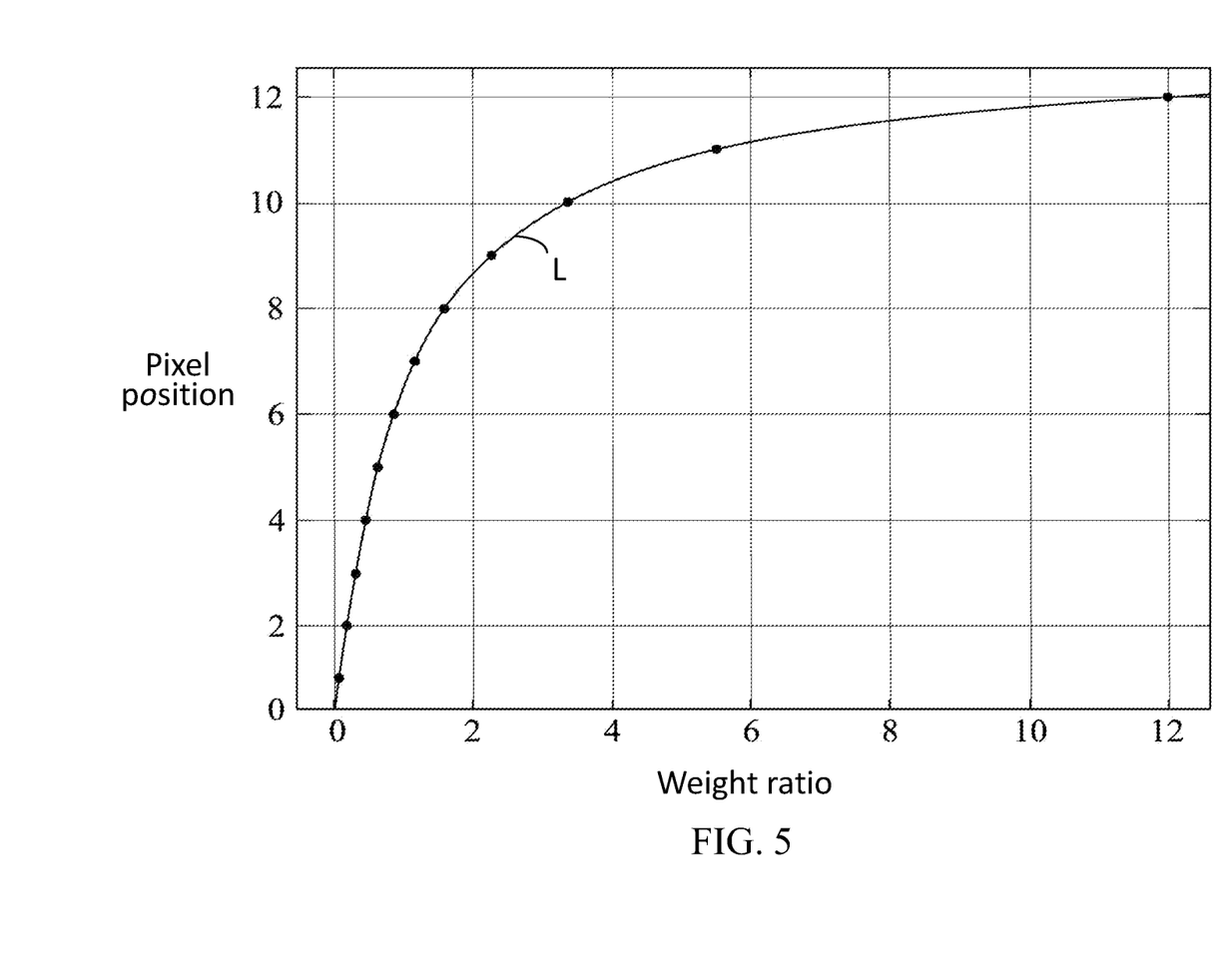
FIG. 5 is a schematic distribution graph of weight ratios vs position centers in another exemplary example in accordance with this disclosure.

As shown in Table 1, equal spacing is assigned to adjacent rows/columns of photoelectric elements of the imaging detector in the X direction, the second column of the table is the reading of the weight provided to the $x^+$ position signal at the center of each row/column in the circuit design of the imaging detector. As shown, the reading in the second column of the table is decreasing linearly from row/column 1 to row/column m (12 in this example), with an increment of −0.0833. In this design, the sum of weights at $x^+$ and $x^-$ of the same position (i.e., listed in the same row/column in the table) is a constant representing the total energy value in the X direction. Similarly, the $x^-$ weight values in the X direction listed in the third column of the table for different positions are linearly increasing, with an increment of 0.0833. Apparently, changes in the $x^-$ and $x^+$ directions are opposite, but the variation of the $x^-/x^+$ weight ratios (listed in the fourth column of the table) demonstrates a curve change in a discrete manner in the corresponding distribution graph, as shown in FIG. 4. In FIG. 4, the horizontal axis is the row/column count in the first column of Table 1 (i.e., the pixel position), and the vertical axis is the weight ratio in the fourth column of Table 1. In this demonstration, the weight ratio is derived by dividing the $x^+$ position weight to the $x^-$ position weight provided respectively to the position center of the photoelectric element in the X direction in the reading circuit design. In other words, to each position center of the specific row/column count, the ratio of the $x^+$ position weight to the $x^-$ position weight in signals is defined to be the weight ratio in the X direction. Similarly, though not shown herein, the ratio of the $y^+$ position weight to the $y^-$ position weight in signals is defined to be the weight ratio in the Y direction. Then, by transposing the aforesaid distribution graph (i.e., FIG. 4), the another distribution graph of the weight ratio vs the position center (i.e., the pixel position) can be obtained, as shown in FIG. 5. In this transposing operation, the horizontal axis of FIG. 4 is transposed to be the vertical axis of FIG. 5, while the vertical axis of FIG. 4 is transposed to be the horizontal axis of FIG. 5. Then, a curve fit is operated upon the distribution of FIG. 5 (i.e., the distribution of the pixel positions to the weight ratios) to obtain a position estimation curve L, as shown in FIG. 5. In this disclosure, the curve fitting is simply a means to explain mathematically the discrete behavior shown in FIG. 4. Since signals for each event outputted from the probe are always processed through the same weight circuit, then the resulted ratio would follow the same behavior of FIG. 4. Thus, in practical operation, the weight ratio of signals in each event is calculated through the the curve-fit function to predict a position for the event. As shown in FIG. 5, the curve-fit function demonstrates to be the position estimation curve L. Similarly, since the same reading circuit design is applied to both the X direction and the Y direction, thus another position estimation curve in the Y direction resembled to that of FIG. 5 can be obtained.

Figure 6A:
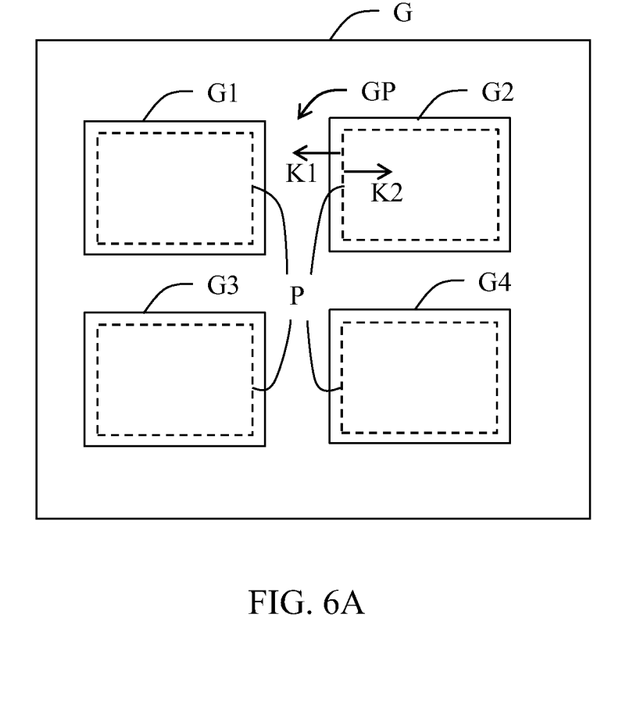
FIG. 6A is a schematic view of an embodiment of the 2D crystal diagram in accordance with this disclosure.
Figure 6B:
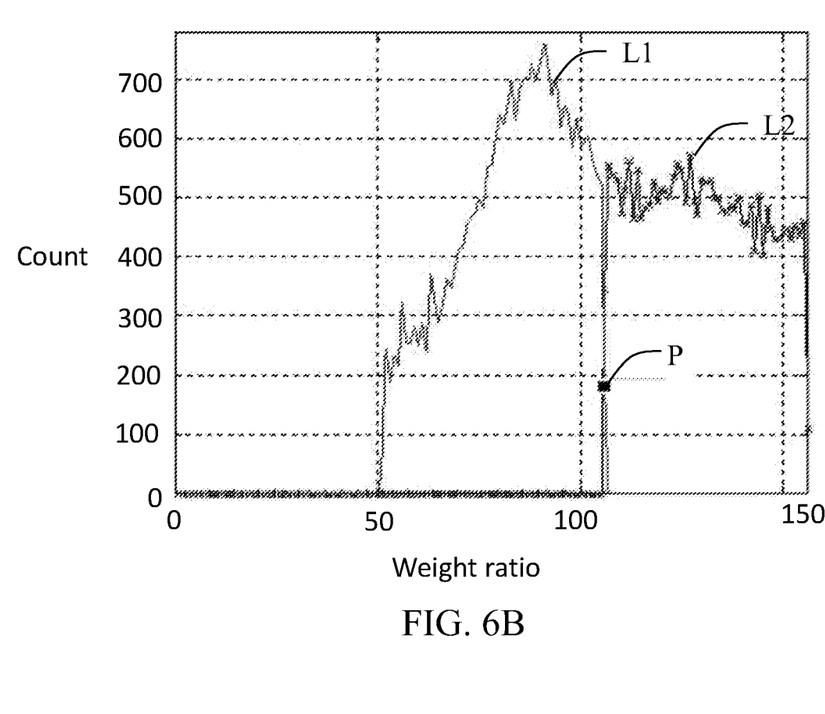
FIG. 6B is a schematic histogram of weight ratios of two columns of crystals with loss in junction areas.

The, transform experimental data for probe calibration (obtained by exposing to a uniform surface radiation source) into a corresponding 2D crystal diagram as the position estimation curve of FIG. 5. In this disclosure, the display manner for the 2D crystal diagram is not limited thereto. Then, a split value for weight ratios of event counts at each of two opposite lateral sides of any junction area in either the X direction or the Y direction in the 2D crystal diagram can be analyzed. In detail, firstly a histogram for the weight ratios is obtained. From this histogram, the split value to determine whether or not a position correction algorithm is necessary to the positions of the incidence events is required. In this disclosure, the junction area can be directed to an area between two adjacent imaging detectors. For example, in the 2D crystal diagram G shown in FIG. 6A, a crystal position G1 is illustrated by a first imaging detector, a crystal position G2 is illustrated by a second imaging detector, a crystal position G3 is illustrated by a third imaging detector, and a crystal position G4 is illustrated by a fourth imaging detector; in which the crystal position G1, the crystal position G2, the crystal position G3 and the crystal position G4 are all disposed with crystals in a predetermined form such as a matrix form. Also, GP is the junction area between the crystal position G1 and the crystal position G2, and that between the crystal position G3 and the crystal position G4. If the crystals at the leftmost column of the crystal position G2 (i.e., the crystals the closest to the junction area GP) meet junction-area loss and require the position-correcting calculation, then the histogram statistics would be performed at the weight ratios ($x^+/x^-$) of the crystals at the two leftmost columns of the crystal position G2. As shown in FIG. 6B, the horizontal axis is the weight ratio (x+/x−), and the vertical axis is the accumulated count of the histogram statistics, which stands for the accumulated count of the gamma-incidence reaction events of the crystals at the two leftmost columns of the crystal position G2 in the 2D crystal diagram. From the histogram results, it can be determined whether or not the incidence-event positions shall need to derive the split values for performing the position correction algorithm. In FIG. 6B, L1 stands for Nogata statistical line of weight ratios for the crystals at the leftmost column, and L2 stands for Nogata statistical line of weight ratios for the crystals at the column next to the leftmost column; i.e., the two Nogata statistical lines L1, L2 the closest to the the junction area. The split value P (threshold value) of the weight ratios is the intersection point of the two Nogata statistical lines. In this embodiment, the split value is 0.106. In other words, in this embodiment, if any weight ratio at the crystal position G2 is smaller than 0.106 (i.e., out of the split-value area, shown as a direction K1 in the crystal position G2 of FIG. 6A. Similarly, the same management of the weight ratios out of the split-value area at the crystal position G2 can be applied to the crystal positions G1, G3 and G4.), then the estimated event positions (obtained from the aforesaid position estimation curve) shall need further corrections. On the other hand (i.e., within the split-value area, shown as a direction K2 in the crystal position G2 of FIG. 6A. Similarly, the same management of the weight ratios within the split-value area at the crystal position G2 can be applied to the crystal positions G1, G3 and G4.), then no correction is necessary. It shall be explained that, practically, L1 and L2 may not intersect to each other at their own zeros. At this time, the split threshold value P would be defined as the average value of the weight ratios at the zeros of the these two statistics lines L1 and L2. Further discussion upon the position-correcting calculation would be elucidated in the following description of the use phase.

Referring back to FIG. 1, after completing the modeling phase, then the use contain the corresponding energy information. When the probe is triggered (i.e., meeting a gamma-ray incidence reaction event), corresponding weight signals would be issued (each of the imaging detectors may contribute four of these weight signals). Then, in the modeling phase, position estimation curves in the X and Y directions can be obtained. By estimating the corresponding positions of the the probe trigger event in the 2D crystal diagram, a position estimation value can be obtained. Then, it is determined whether or not the corresponding weight ratio falls within the split-value area. If the determination is positive, then no position-correcting calculation is required, and the position estimation value for the event would be accounted to the corresponding position of the respective probe in the 2D crystal diagram so as to derive the position value. Thereafter, a crystal code corresponding to this position value would be located in a crystal-code look-up table (cLUT), ans an energy code corresponding to the energy value would be located in an energy-window look-up table (eLUT). The crystal code and the energy code are the necessary data for carrying out the image-reconstructing calculation as follows. The cLUT and the eLUT are established from the experimental data for calibration obtained through the exposure by the uniform planar radiation source, which is widely used in the conventional technology and thus details thereabout are omitted herein. On the other hand, if the determination is negative, then it is determined that the corresponding weight ratio falls out of the split-value area (i.e., in the GP of FIG. 6A). Thus, the position-correcting calculation would be performed upon the position value to utilize energy values of the adjacent imaging detectors to correct the position estimation value. According to this disclosure, two algorithms for the position-correcting calculation are provided. One of them is a Δx correction algorithm, the equation thereto is listed as follows.

$$X_{s1'} = X_{s1} + \frac{E_{s2}}{(E_{s1} + E_{s2})} \times (\text{region pixel}). \quad (3)$$

In equation (3), $X_{s1'}$ is the corrected position value of the imaging detector in the X direction, and $X_{s1}$ is the original position value (obtained from the position value of the imaging detector in the X direction through analyzing the position estimation curve). The term $$\frac{E_{s2}}{(E_{s1} + E_{s2})} \times (\text{region pixel})$$

is the Δx, in which $E_{s1}$ is the energy value of the imaging detector S1, and $E_{s2}$ is the energy value of the imaging detector S2. Namely, the energy value of an imaging detector and the energy value of another imaging detector adjacent to the imaging detector are utilized to correct the position estimation value, such that the disperse energy values close to the cross over region (i.e., GP in FIG. 6A) can be collected to perform the position-correcting calculation. The "(region pixel)", a predetermined constant, is the number of spatial units to represent a photonic pixel in the 2D crystal diagram. For example, in this embodiment shown in FIG. 3, the "(region pixel)" is 20. However, in this disclosure, this constant can be adjusted according to practical situations such as the crystal size or the resolution of detector. If the position to be corrected is the y position, then equation (3) can be also applied to provide a correction value Δy, with the energy values of the adjacent detectors to meet instant situations. In an exemplary example, if the y position to be corrected belongs to an imaging detector, then the energy value of the adjacent detector is $E_{s3}$, and Δy would be $$\frac{E_{s3}}{(E_{s1} + E_{s3})} \times (\text{region pixel}).$$

Accordingly, the 2D crystal diagram for the entire probe can be corrected at GP of FIG. 6A.

Nevertheless, this disclosure is not limited thereto. Another algorithm for the position-correcting calculation is an energy-weight modification as follows.

$$X_{s1'} = \frac{E_{s1} * X_{s1} + E_{s2} * X_{s2}}{E_{s1} + E_{s2}}. \quad (4)$$

The algorithm of equation (4) is to define energy values of two detectors as the weights for modifying the estimated positions. Similarly, if the position to be corrected is the y position, then energy values of adjacent detectors shall be modified. In this exemplary example, if the y position to be corrected belongs to the imaging detector, then the energy value of one adjacent detector is $E_{s3}$, and the corrected y position $Y_{s1'}$ should be equal to $$\frac{E_{s1} * Y_{s1} + E_{s3} * Y_{s3}}{E_{s1} + E_{s3}}.$$

Accordingly, the 2D crystal diagram for the entire probe can be corrected at GP of FIG. 6A.

By applying any one of the aforesaid two position-correcting calculations, then the crystal with the junction-area loss can be reconstructed in the 2D crystal diagram. Thereupon, the imaging probe formed by a plurality of imaging detectors can be reconstructed to have a continuous and complete imaging area, and simultaneously a consistent resolution (or crystal size) can be maintained.

Then, the position in the 2D crystal diagram for the event-position estimated value corresponding to the probe is yet to be determined. In addition, by having the position value and the energy value to be checked in the crystal code look-up table (cLUT) and the energy window look-up table (eLUT), respectively, to locate the corresponding crystal and energy codes, then the image-reconstructing calculation can be further performed to obtain the corresponding tomography data.

It shall be explained that the position decoding algorithm of this disclosure is not to follow a conventional algorithm of Anger's logic. In the conventional algorithm of Anger's logic, the energy value is utilized to estimate the event position. If this conventional algorithm is applied to the imaging probe formed by semiconductor photoelectric elements, since such type of devices is too temperature-sensitive to obtain a stable total energy value, thus the corresponding 2D crystal diagram would be deformed, and so the crystal code determined from the cLUT would meet inevitable errors. Thereupon, the performance of the entire imaging output would be unstable, and thus the corresponding performance and practicality of the probe components could be reduced. In the position-decoding algorithm provided by this disclosure, the weight ratio is utilized to derive the estimated event position, and the corresponding position estimation curve is formed by the weights of the reading circuits so as not to be effected by temperatures of the photoelectric elements. In current development of gamma imaging probes and the corresponding application documents, such a temperature-sensitive semiconductor-type photoelectric element is one of the mainstream components. The technology provided in this disclosure can solve the temperature sensitivity problem to a considerable extent, and thus the performance, practicability and market competitiveness of the probe components can be substantially enhanced.

Figure 7:
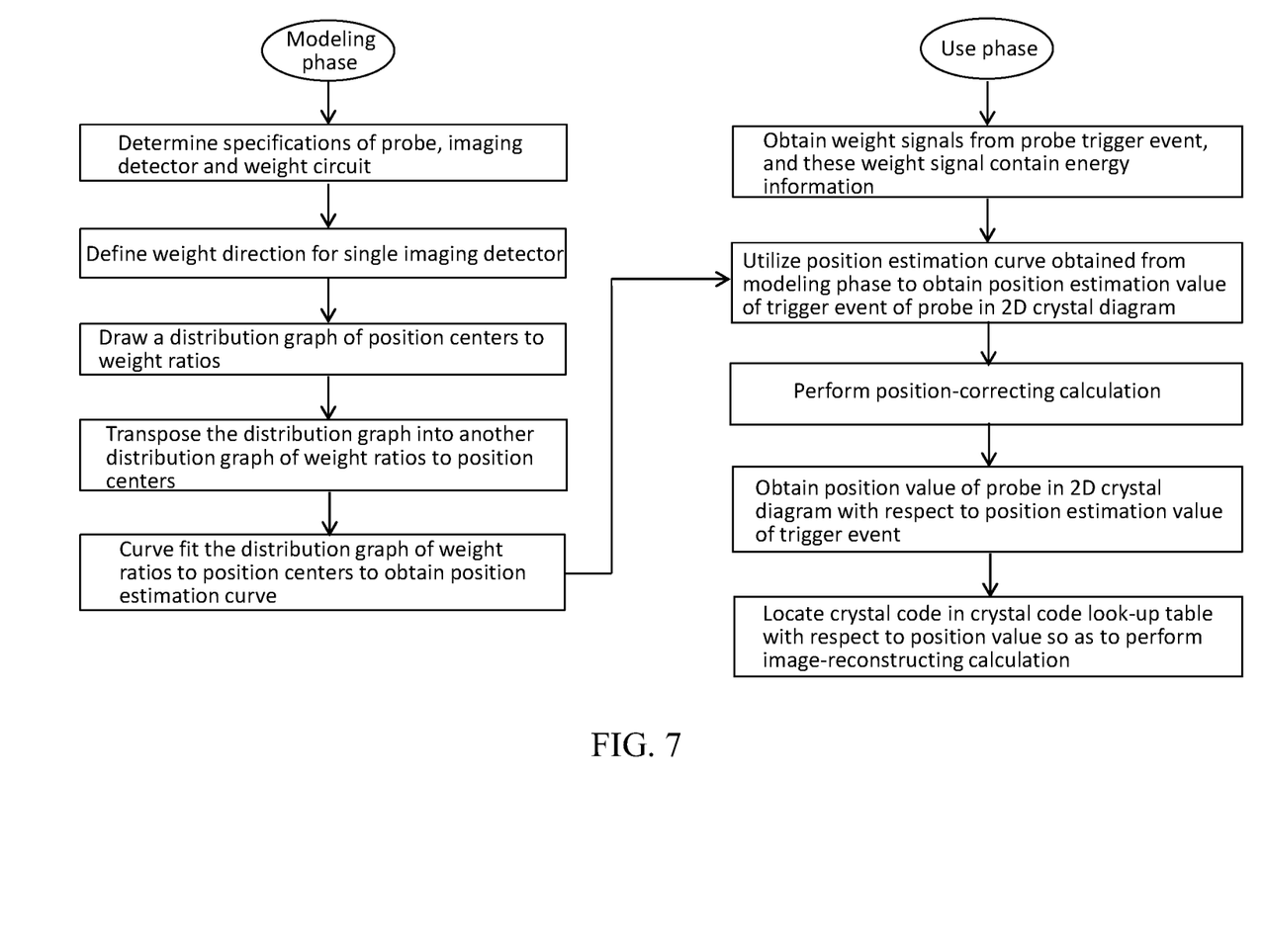
FIG. 7 is a schematic flowchart of another embodiment of the position-signal processing method for flat panel gamma imaging probe in accordance with this disclosure.

FIG. 7 is a schematic flowchart of another embodiment of the position-signal processing method for flat panel gamma imaging probe in accordance with this disclosure. As shown, the method of this embodiment is applicable to application conditions of high-resolution algorithm for pixel dimensions with a 1.1 mm×2.7 mm crystal size. Since the flowchart of FIG. 7 is roughly similar to that of FIG. 1, thus the same steps can be referred to the corresponding explanation elucidated from FIG. 1 through FIG. 6B, and details thereabout would be omitted herein. A major difference between FIG. 7 and FIG. 1 is that, in FIG. 7, the the modeling phase is ended after the distribution graph of the weight ratios and position centers is curve fitted to obtain the corresponding position estimation curve with respect to the weight ratio. Namely, in the embodiment of FIG. 7, no further work is required to utilize the position estimation curve to transform the experimental data for probe calibration into the 2D crystal diagram, and the step of analyzing the 2D crystal diagram to obtain the split values corresponding to the weight ratios of the lateral events within the junction areas in either the X direction or the Y direction is also removed. In the aforesaid embodiment shown in FIG. 1, these two omitted steps are used to obtain the split threshold values P for telling whether the position estimation value is located within a correction-required area (i.e., out of the split-value area, direction K1 in FIG. 6A) or within a correction-not-required area (i.e., within the split-value area, direction K2 in FIG. 6A). If the estimated event position is within the correction-required area, then the position value shall be corrected by undergoing the aforesaid position-correcting calculation. The major purpose for dividing and determining the areas is at the concern of resolution (i.e., the crystal size). In a super high resolution situation, if the crystal size is less than ⅓ of the photonic pixel size (in this embodiment, the photo-sensing element has a size of 3.3 mm, and thus the super high resolution is directed to the crystal size less than 1.1 mm), the count cloud of the crystal in the 2D crystal diagram would be too fine to reduce electronic noise factors in performing the aforesaid position-correcting calculation. Thereupon, the count cloud of the crystal would be wider, and the associated vision effect would be vague, such that the expected super high resolution would be sacrificed. Hence, the determination of the correction-required area ans the correction-not-required area is necessary.

As such, the position-correcting calculation is only applied to the event positions within the correction-required area, not the those within the correction-not-required area, and thus the super high resolution can be maintained. This is the algorithm logic of the embodiment shown in FIG. 1. On the other hand, in FIG. 7, the high resolution situation is considered. When the crystal size is ranged between ⅓ and ⅘ of the photonic pixel size (I.e., between 1.1 mm and 2.7 mm of the crystal size), the count cloud of the crystal distributed in the 2D crystal diagram would be less sensitive to the noises introduced by the position-correcting calculation, and no difference can be located through naked eyes. Thus, the position-correcting calculation can be performed to the entire probe region, and no need to perform division operation in the modeling phase, such that labor and time spent within the modeling phase can be substantially reduced in analyzing the split threshold value P. In addition, in the use phase, the step of determining whether or not e weight ratio is fallen within the split-value area in no longer necessary before the position-correcting calculation is performed upon each of the estimated positions.

Figure 8:
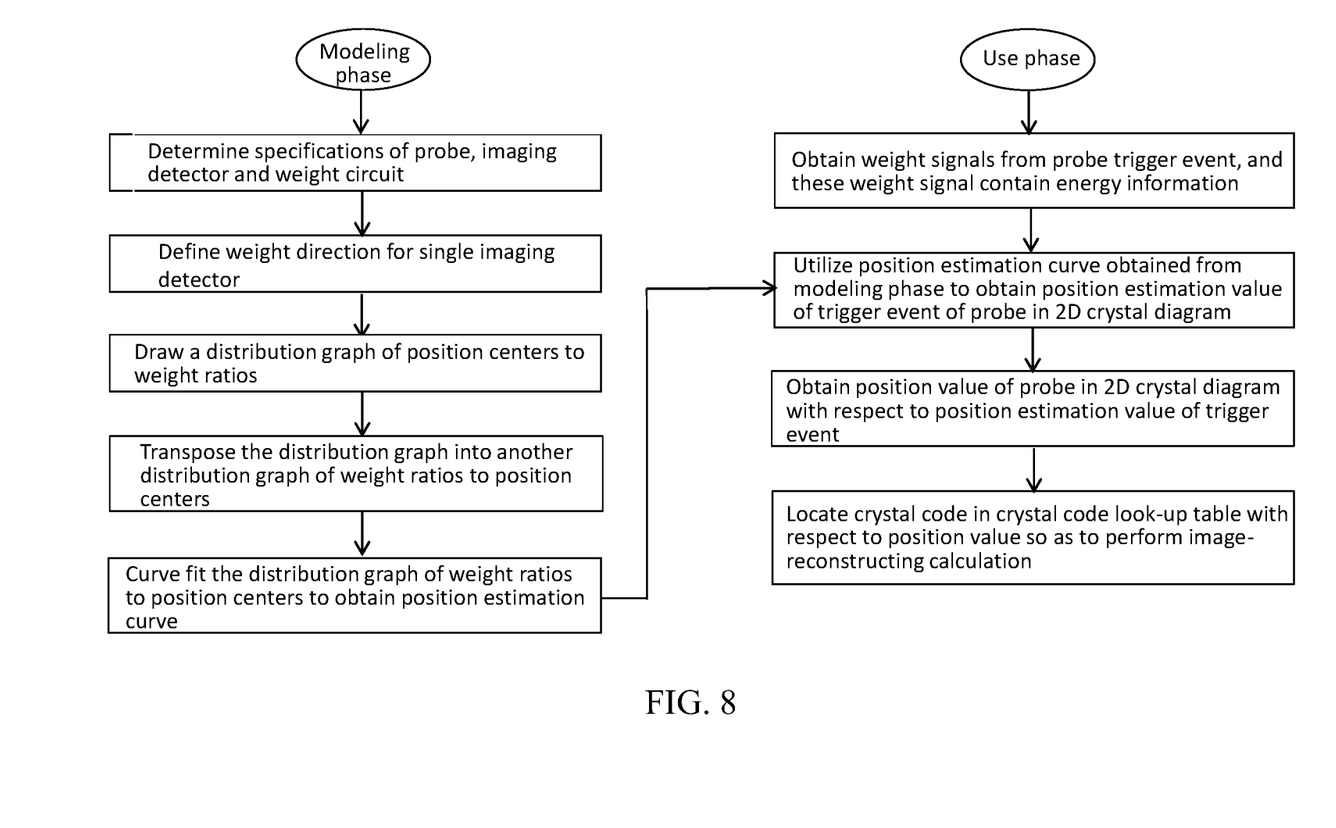
FIG. 8 is a schematic flowchart of a further embodiment of the position-signal processing method for flat panel gamma imaging probe in accordance with this disclosure.

FIG. 8 is a schematic flowchart of a further embodiment of the position-signal processing method for flat panel gamma imaging probe in accordance with this disclosure. As shown, the method of this embodiment is applicable to application conditions of middle-resolution algorithm for pixel dimensions with a crystal size larger than 2.7 mm. According to aforesaid research experience, while in considering the situation of middle resolution whose crystal size is larger than ⅘ of the photonic pixel size (I.e., the crystal size is larger than 2.7 mm), each of the crystals can cover almost an entire photo-sensing element (70% or more). Thus, to those crystals at the boundary of the imaging detector, the energy percentage lost to the adjacent detector is usually less than 5%, and the influence upon the position estimation can be neglected. Thus, in this embodiment, beside that the modeling phase does not perform an analysis upon the split threshold values, the use phase does not carry out the position-correcting calculation. As shown, the method of this embodiment is applicable to application conditions of high-resolution algorithm for pixel dimensions with a 1.1 mm×2.7 mm crystal size. Since the flowchart of FIG. 8 is roughly similar to that of FIG. 1 or FIG. 7, thus the same steps can be referred to the corresponding explanation elucidated from FIG. 1 through FIG. 6B, and details thereabout would be omitted herein. A major difference between FIG. 8 and FIG. 7 is that, in FIG. 8, the use phase requires no position-correcting calculation.

In summary, in the position-signal processing method for flat panel gamma imaging probe provided by this disclosure, the position decoding algorithm does not follow the conventional technology (i.e., Anger's logic), and the problem of discontinuous imaging in the junction area of the adjacent imaging detectors in the conventional technology can be resolved. Thereupon, the entire imaging area can be complete, continuous and consistent in maintaining the high resolution.

In addition, the position-signal processing method for flat panel gamma imaging probe provided by this disclosure can lessen the temperature-sensitive effect, and can stabilize the high-performance output of the imaging probe assembly.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A position-signal processing method for flat panel gamma imaging probe, comprising the steps of:
in a modeling phase,
defining a weight direction for a single imaging detector;
according to position centers and weight ratios of the single imaging detector in an X direction and a Y direction of the weight direction to obtain a distribution graph of the weight ratios with respect to the position centers; and
performing curve fitting upon the distribution graph of the weight ratios with respect to the position centers to obtain a position estimation curve related to the weight ratios; and
in a use phase,
utilizing the position estimation curve obtained in the modeling phase to derive a position estimation value of a trigger event of a probe in a 2D crystal diagram;
obtaining a position value of the probe in the 2D crystal diagram with respect to the position estimation value of the trigger event; and
locating a crystal code in a crystal code look-up table with respect to the position value of the probe in the 2D crystal diagram for a following image-reconstructing calculation.

2. The position-signal processing method for flat panel gamma imaging probe of claim 1, prior to the step of obtaining the position value of the probe in the 2D crystal diagram with respect to the position estimation value of the trigger event, further including a step of performing a position-correcting calculation upon the position value.

3. The position-signal processing method for flat panel gamma imaging probe of claim 2, wherein the position-correcting calculation is performed upon an energy value of the single imaging detector and an energy value of an imaging detector adjacent to the single imaging detector.

4. The position-signal processing method for flat panel gamma imaging probe of claim 2, wherein the position-correcting calculation includes a $\Delta x$ correction algorithm expressed as:

$$X_{s1'} = X_{s1} + \frac{E_{s2}}{(E_{s1}+E_{s2})} \times (\text{region pixel})$$

wherein $X_{s1'}$ stands for the position value of the single imaging detector after the position-correcting calculation, $X_{s1}$ stands for the position value of the single imaging detector obtained from the position estimation curve, $$\frac{E_{s2}}{(E_{s1}+E_{s2})} \times (\text{region pixel})$$

stands for a $\Delta x$, $E_{s1}$ stands for the energy value of the single imaging detector, and $E_{s2}$ stands for the energy value of the another imaging detector adjacent to the single imaging detector.

5. The position-signal processing method for flat panel gamma imaging probe of claim 2, wherein the position-correcting calculation includes an energy-weight modification expressed as:

$$X_{s1'} = \frac{E_{s1}*X_{s1}+E_{s2}*X_{s2}}{E_{s1}+E_{s2}}$$

wherein $X_{s1'}$ stands for the position value of the single imaging detector after the position-correcting calculation, $X_{s1}$ stands for the position value of the single imaging detector obtained from the position estimation curve, $E_{s2}$ stands for the energy value of the single imaging detector, and $E_{s2}$ stands for the energy value of the another imaging detector adjacent to the single imaging detector.

6. The position-signal processing method for flat panel gamma imaging probe of claim 2, prior to the step of performing the position-correcting calculation upon the position value, further including the steps of:
determining whether or not a weight ratio falls within a split-value area;
if negative, performing the position-correcting calculation upon the position value; and
if positive, obtaining the position value of the probe in the 2D crystal diagram with respect to the position estimation value of the trigger event.

7. The position-signal processing method for flat panel gamma imaging probe of claim 6, after the step of obtain the position estimation curve related to the weight ratios, further including a step of utilizing the position estimation curve to transform experimental data for probe calibration into the 2D crystal diagram.

8. The position-signal processing method for flat panel gamma imaging probe of claim 7, after the step of utilizing the position estimation curve to transform the experimental data for probe calibration into the 2D crystal diagram, further including a step of analyzing split values of weight ratios for corresponding events lateral to junction areas in the 2D crystal diagram in the X direction or the Y direction, wherein the junction areas are junction portions between the single imaging detector and the another imaging detector.

9. The position-signal processing method for flat panel gamma imaging probe of claim 8, wherein the step of analyzing split values of weight ratios for corresponding events lateral to junction areas in the 2D crystal diagram in the X direction or the Y direction further includes the steps of:
   performing a histogram statistics upon the weight ratios of crystals located the closest and secondary closest to the junction areas so as to obtain two Nogata statistical lines corresponding to the crystals located the closest and secondary closest to the junction areas, respectively; and
   defining an intersection point of the two Nogata statistical lines as the split value for the weight ratios.

10. The position-signal processing method for flat panel gamma imaging probe of claim 1, prior to the step of defining the weight direction for the single imaging detector, further including a step of determining specifications of the probe, the single imaging detector and a weight circuit.

11. The position-signal processing method for flat panel gamma imaging probe of claim 10, wherein the step of determining the specifications of the probe, the single imaging detector and the weight circuit is performed by adopting a gamma-ray detector as the imaging detector, the gamma-ray detector is consisted of a plurality of scintillating crystals arranged in a matrix form, and the weight circuit of the single imaging detector is a circuit capable of reading bidirectional signals in the X direction and the Y direction.

12. The position-signal processing method for flat panel gamma imaging probe of claim 1, wherein the step of according to the position centers and the weight ratios of the single imaging detector in the X direction and the Y direction of the weight direction to obtain the distribution graph of the weight ratios with respect to the position centers includes the steps of:
   forming the distribution graph of the weight ratios with respect to the position centers of the single imaging detector in the X direction and the Y direction; and
   transposing the distribution graph of the weight ratios with respect to the position centers to obtain another distribution graph of the position centers with respect to the weight ratios.

13. The position-signal processing method for flat panel gamma imaging probe of claim 12, wherein the step of forming the distribution graph of the weight ratios with respect to the position centers of the single imaging detector in the X direction and the Y direction further includes the steps of:
   each of gamma incidence events generating $x^+$, $x^-$, $y^+$ and $y^-$ position signals, energy information of the each of gamma incidence events being formed by adding all the $x^+$, $x^-$, $y^+$ and $y^-$ position signals;
   reading weights of the $x^+$, $x^-$, $y^+$, $y^-$ position signals of individual photoelectric elements provided by the weight circuit of the single imaging detector; and
   dividing each of the $x^+$ position signals by the corresponding $x^-$ position signal so as to obtain the weight ratio in the X direction, and dividing each of the $y^+$ position signals by the corresponding $y^-$ position signal so as to obtain the weight ratio in the Y direction.

14. The position-signal processing method for flat panel gamma imaging probe of claim 1, prior to the step of obtaining the position value of the probe in the 2D crystal diagram with respect to the position estimation value of the trigger event, further including a step of obtaining a weight signal from the probe trigger event, wherein the weight signal contains energy information.

\* \* \* \* \*